United States Patent [19]

Souma

[11] Patent Number: 5,137,024
[45] Date of Patent: Aug. 11, 1992

[54] GAS FLOW VALVE AND SPHYGMOMANOMETER AIR-FEEDING/DISCHARGING APPARATUS USING THE SAME

[75] Inventor: Takahiro Souma, Nakai, Japan

[73] Assignee: Terumo Kabushiki Kaisha, Tokyo, Japan

[21] Appl. No.: 591,753

[22] Filed: Oct. 2, 1990

[30] Foreign Application Priority Data

Oct. 6, 1989 [JP] Japan .................................. 1-260196

[51] Int. Cl.⁵ ..................... A61B 5/0235; F16K 15/14
[52] U.S. Cl. ................................ 128/685; 137/513.5; 137/847
[58] Field of Search ..................... 128/672, 677, 685; 137/513.3, 513.5, 846, 850, 851, 845, 847; 251/117, 205

[56] References Cited

U.S. PATENT DOCUMENTS

| Re. 32,587 | 2/1988 | Matsuura et al. | 128/685 |
|---|---|---|---|
| 3,901,272 | 8/1975 | Banners et al. | 137/846 X |
| 4,130,114 | 12/1978 | Peeler | 128/677 |
| 4,198,031 | 4/1980 | Ezekiel | 251/117 |
| 5,027,823 | 7/1991 | Sanaka | 128/685 |

FOREIGN PATENT DOCUMENTS

2759119 12/1977 Fed. Rep. of Germany .
61-142003 9/1986 Japan .
993002 9/1962 United Kingdom .

*Primary Examiner*—Lee S. Cohen
*Assistant Examiner*—Kevin Pontius
*Attorney, Agent, or Firm*—Frishauf, Holtz, Goodman & Woodward

[57] ABSTRACT

A gas flow valve enables constant venting and is used with a cuff showing a rapid decrease in venting ability at a predetermined value on a boundary within the pressure range which allows measurment of blood pressure. The gas flow valve has a body made of an elastic material and comprising a wedge-shaped portion formed integrally with a mounting base so as to have a flat portion with upper and lower surfaces serving as pressure-responsive surfaces, a linear opening formed at the tip of the wedge-shaped portion, and a passageway communicating with the opening and extending in the longitudinal direction within the mounting base and the tip portion. A thin sheet-like member is twisted and disposed in the passageway so that the tip portion is held by the opening. As a result, the elastic deformation of the gas passageway formed by the gaps in the opening during pressure reduction is promoted by the resiliency of the torsion of the thin sheet-like member. A sphygmomanometer air-feeding/discharging apparatus with the gas flow valve has flexibility for cuffs having various shapes and specifications and enables easy adjustment of the orifice area.

20 Claims, 8 Drawing Sheets

GAS FLOW VALVE AND SPHYGMOMANOMETER AIR-FEEDING/DISCHARGING APPARATUS USING THE SAME

BACKGROUND OF THE INVENTION

1. Field of the Invention

This invention relates to a gas flow valve and a sphygmomanometer air-feeding/discharging apparatus using the valve.

2. Description of the Prior Art

A conventional gas flow valve will be described with reference to the drawings. FIG. 10 is a perspective view of the appearance of a conventional gas flow valve. The gas flow valve shown in FIG. 10 is shown in FIG. 3 in the specification of Japanese Utility Model Application Laid-Open (KOKAI) No. 61-142003 filed by the present applicant.

In FIG. 10, a thin sheet-like member 30, which has a convex form and is called "flapper", functions as a body for regulating the amount of leakage of a gas flow. This convex thin sheet-like member comprises a substantially T-shaped thin piece made of plastic or the like base end of which has vanes 30a projecting to the left and right at right angles to the longitudinal direction of the member 30. Each of the vanes 30a has a shape and dimensions that enable the vanes 30a to fit into grooves 34 formed in a main body 32 of the gas flow valve. The longitudinal dimension of the thin sheet-like member 30 is such that, when the vanes 30a are respectively fitted into the grooves 34, the distal end of the member 30 will pass through a linear opening 38 provided in one end of the main body 32, as shown in the drawing.

When the thin sheet-like member 30 is mounted in an air passageway 36 of the main body 32, the linear opening 38 is opened so that gaps 40 are formed on both sides of the thin sheet member 30. As a result, venting takes place through the gaps 40. The main body 32 has a flat portion 32a having upper and lower surfaces serving as pressure-responsive surfaces so as to discharge air while changing the orifice area of each of the gaps 40 in response to a change in the cuff pressure acting on the flat portion 32a.

FIG. 4 shows a relation between the cuff pressure and the orifice opening area and the cuff venting ability. In the drawing, a characteristic curve B partially denoted by a broken line shows the orifice opening area of the above-mentioned conventional gas flow valve and shows that the orifice opening area substantially linearly changes within the range of cuff pressure from 250 mmHg at the highest to 0 mmHg.

A characteristic curve H denoted by a one-dot chain line shows the venting ability of a cuff made of an elastic material such as rubber or the like. As shown in the drawing, the venting ability rapidly decreases as the cuff pressure increases from 60 mmHg. This is attributed to the material and shape of the cuff.

On the other hand, a throttle valve is provided near the air-feeding outlet of a sphygmomanometer air-feeding bulb for the purpose of determining an appropriate pressure reduction rate with which the pressure is gradually reduced for measuring blood pressure during the reduction in cuff pressure. The throttle valve has a fixed orifice or a simple structure which enables the adjustment of the throttle valve. In the latter simple structure, the screw 100 shown by a two-dot chain line in FIG. 10 is screwed into a body (not shown) in order to enable the adjustment of the throttle valve, and the linear opening 38 of the gas flow valve 32, which is provided between the cuff and the air-feeding bulb, is pressed by the screw 100 in the transverse direction so that the minimum orifice area is set.

However, the conventional gas flow valve configured as described above includes a problem in that, when it is used in combination with a cuff having the venting ability shown by the characteristic curve H in FIG. 4, the venting rate, i.e., the pressure reduction rate, is rapidly decreased within the pressure range of from 60 to 0 mmHg, which yet allows measurement of blood pressure, and this makes constant venting impossible.

The throttle valve provided in a sphygmomanometer air-feeding/discharging apparatus using the conventional gas flow valve includes a problem in that, when it has a fixed orifice, as described above, it has no flexibility for cuffs having various shapes and specifications.

When the linear opening of the gas flow valve is pressed directly by the screw in the transverse direction for the purpose of regulating the throttle valve, there is a problem in that the orifice area is not constant, and thus the adjustment cannot be easily made. In addition, even if the pressure reduction characteristics of a constant rate discharge valve are adjusted to ideal state conditions which agree with the venting characteristics of the cuff connected to the valve, there is a problem in that the initial pressure reduction characteristics cannot be secured owing to differences in compliance with the cuff used.

SUMMARY OF THE INVENTION

Accordingly, a gas flow valve and a sphygmomanometer air-feeding/discharging apparatus using the valve in accordance with the present invention have been achieved in consideration of the above-described problems, and it is an object of the present invention to provide a gas flow valve which enables constant venting and allows the use of a cuff showing a rapid decrease in venting ability from a predetermined pressure value at a boundary within a pressure range which allows measurement of blood pressure.

It is another object of the present invention to provide a sphygmomanometer air-feeding/discharging apparatus which has flexibility for cuffs having different shapes and specifications and which allows easy adjustment of the orifice area.

It is still another object of the present invention to provide a gas flow valve which permits easy adjustment of the orifice area.

In order to achieve the objects, a gas flow valve in accordance with the present invention comprises a body made of an elastic material and comprising a mounting base, a wedge-shaped portion which is formed integrally with the mounting base and which has a flat portion with upper and lower surfaces serving as pressure-responsive surfaces, a linear opening formed at the tip of the wedge-shaped portion, and a passageway extending longitudinally within the mounting base and the tip portion and communicating with the opening; and a thin sheet-like member having a tip end portion and a rear end fitting portion and disposed in the passageway in such a manner that the tip end portion is held by the opening; wherein the thin sheet-like member is twisted and held by engaging the rear end fitting portion with the mounting base so that the elastic deformation of the gas flow orifices formed by the gaps in the opening can be promoted by the resiliency of the torsion of the thin sheet-like member when the cuff pressure is reduced.

In a preferred embodiment, a sphygmomanometer air feeding/discharging apparatus for feeding and discharging air to and from a cuff comprises an air feeding bulb, a gas flow valve according to claim 1 which is connected to the air-feeding outlet of the air-feeding bulb, a discharge valve interposed between the cuff and the gas flow valve for the purpose of manually forcing air to discharge, and a throttle valve interposed between the cuff and the discharge valve for the purpose of gradually reducing pressure and regulating a pressure reduction rate by regulating the throttle valve when blood pressure is measured during a reduction in the cuff pressure.

In a preferred embodiment, a gas flow valve comprises a body comprising a mounting base, a tip base which is formed integrally with the mounting base and which has a wedge-like outer shape having a flat portion with upper and lower surfaces serving as pressure-responsive surfaces, a linear opening formed in the side end of the tip base, a first passageway communicating with the opening and extending longitudinally within the mounting base and the tip base, and a fitting hole formed at the rear end of the mounting base so as to be open at one end thereof; and a thin sheet-reduction like member formed integrally with a fitting member which is inserted in the fitting hole of the body and securely fitted therein and which has a second passageway communicating with the first passageway at its one end; wherein, when the thin sheet-like member is twisted and disposed in the first passageway, the fitting member is fitted rotatably in the direction of the torsion angle so that the torsion angle of the thin sheet-like member can be adjusted.

In a preferred embodiment, the thin sheet-like member comprises a resin sheet material having heat resistance for preventing permanent deformation, which is caused by a temperature change.

In a preferred embodiment, a frictional fitting surface is formed in the fitting member so that the torsion angle of the thin sheet-like member twisted and held by the opening at the tip portion can be adjusted, and recessed portions are formed in the end surface opposite to the side of the fitting member to which the thin sheet-like member is attached so that a turning force is applied to the recessed portions during the adjustment of the torsion angle.

In a preferred embodiment, flexibility is secured for combination with various air-feeding bulbs for feeding and discharging air to and from a gas flow valve and a cuff.

In order to achieve the objects, various other obvious modifications can be made within the scope of the claims.

DESCRIPTION OF THE PREFERRED EMBODIMENTS

Embodiments of the present invention will be described in detail with reference to the drawings.

Figure 1:
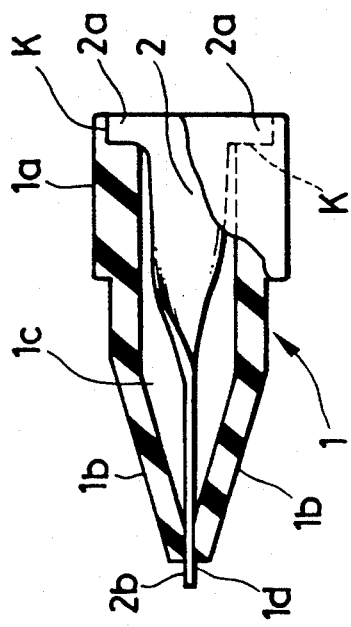
FIG. 1 is a partially broken-out sectional view taken along a line passing through the central surface of a gas flow valve of an embodiment according to the present invention.
Figure 2:
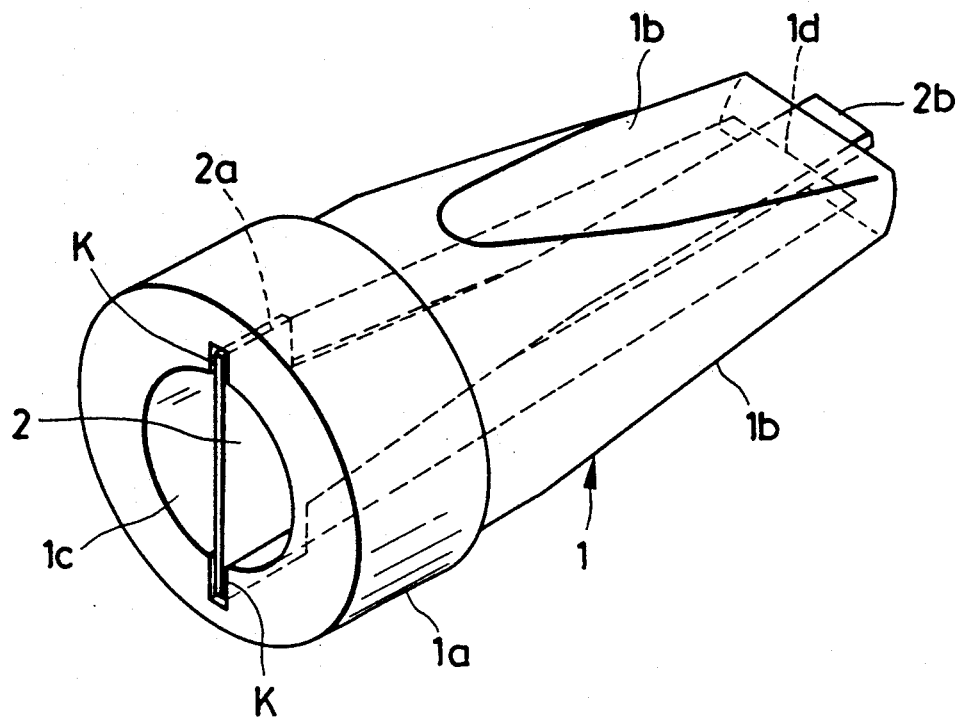
FIG. 2 is a perspective view of the appearance of the gas flow valve shown in FIG. 1.

FIG. 1 is a partially broken-out sectional view taken along a line passing through the central surface of a gas flow valve of an embodiment, and FIG. 2 is a perspective view of the gas flow valve shown in FIG. 1. In both drawings, the body 1 of the gas flow valve is made of silicone rubber having rubber hardness of about 40 (according to Hardness Testing Method described in Japanese Industrial Standard K6301) and is formed integrally with a mounting base 1a into a wedge-like shape having flat surfaces 1b on both sides thereof. As shown in the drawings, an air passageway 1c extending along substantially the axis of the body 1 is open at one end in the mounting base 1a and has at the other end a linear slit, i.e., a linear opening 1d, communicating with the air passageway 1c.

The flat surfaces 1b of the wedge-shaped portion of the body 1 serve as pressure-responsive surfaces. As a result of conversion of the flat surfaces 1b by the cuff pressure described below, the area of each of the orifices formed in the linear opening 1d is changed. On the other hand, a thin sheet-like member 2 used in combination with the body 1 is obtained by cutting out the outline from a resin thin sheet having spring properties, such as a polycarbonate sheet, a polypropylene sheet of the like, a phosphor bronze thin sheet or a stainless thin sheet used for springs. As shown in the drawings, the thin sheet-like member 2 has at its one end vanes 2a which extend transversely at right angles to the longitudinal direction of the body 1. The vanes 2a of the thin sheet-like member 2 are fitted in the grooves K provided in the mounting base 1a. The tip portion 2b of the thin sheet-like member 2 is held by the opening 1d of the body 1, as shown in the drawings. Since the thin sheet-like member 2 is twisted for about 90 degrees, a torsion returning force of the thin sheet-like member 2 to return to the original plate shape is constantly applied to the opening 1d of the body 1.

Figures 3A, 3B, 3C:
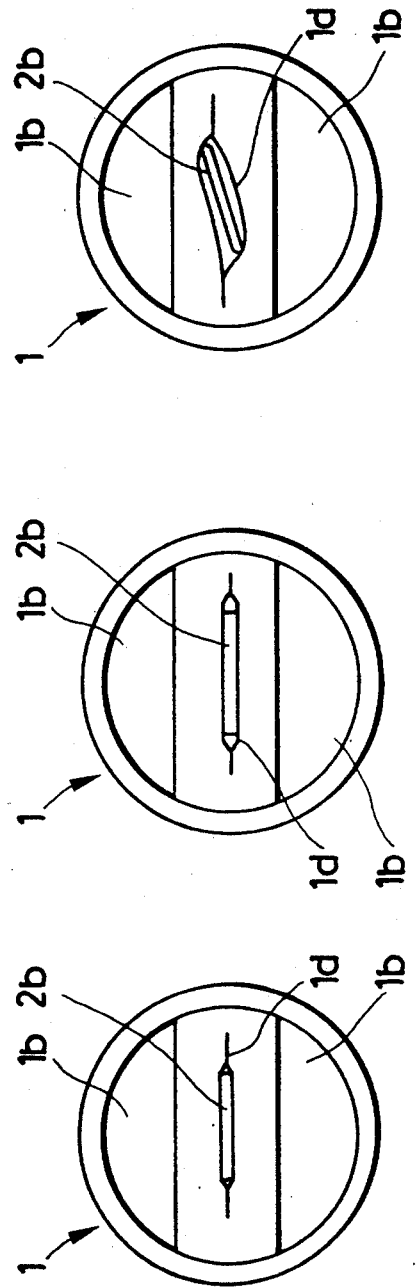
FIGS. 3A, 3B and 3C are left-side views of the gas flow valve shown in FIG. 1 which are provided for explaining the operation thereof.
Figure 4:
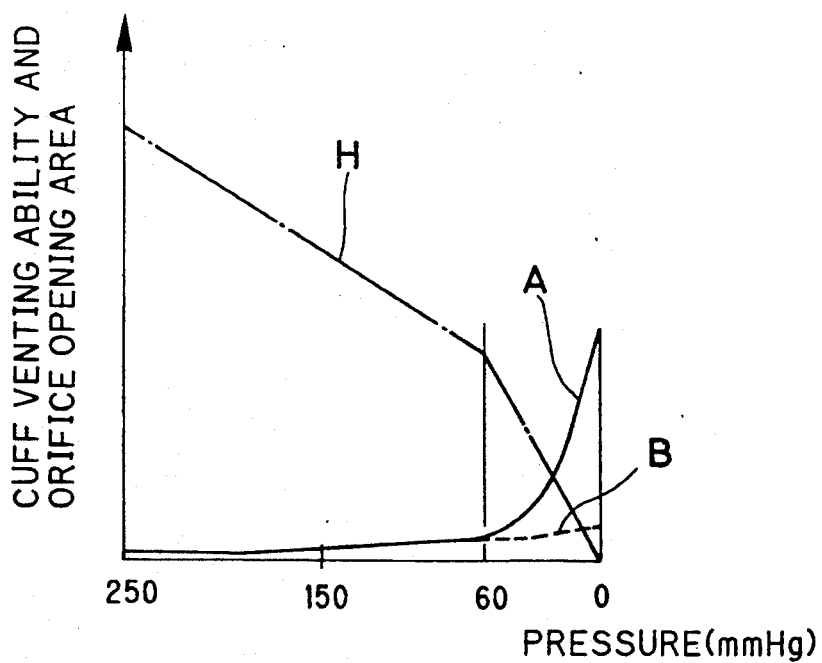
FIG. 4 is a drawing showing a relation between the cuff pressure, the orifice opening area and the cuff venting ability.

FIGS. 3A, 3B and 3C are left-side views of the gas flow valve shown in FIG. 1 which are provided for explaining the operation thereof. FIG. 3A shows a state where pressure, which is reduced from 250 mmHg to 150 mmHg, is applied to the flat surfaces 1b of the body 1. Since triangular orifices, which are defined by the height of the tip portion 2b of the thin sheet-like member 2 held by the opening 1d, are formed, the state shown in FIG. 3A corresponds to a linear portion within the pressure range of 250 mmHg to 150 mmHg of the characteristic curve A in FIG. 4 which indicates changes in orifice opening area.

FIG. 3B shows a state where pressure of 150 mmHg to 60 mmHg is applied to the flat surfaces 1b of the body 1. As a result of a reduction in pressure acting on the flat surfaces, semiellipsoidal orifices, each of which has a side defined by the height of the tip portion 2b of the thin sheet-like member 2 held by the opening 1d, are formed by the elastic returning force possessed by the body 1, as shown in the drawing. This state corresponds to a linear portion within the pressure range of from 150 mmHg to 60 mmHg of the characteristic curve A in FIG. 4 which indicates changes in orifice opening area.

FIG. 3C shows a state where pressure reduced from 60 mmHg to 0 mmHg is applied to the flat surfaces 1b of the body. In this state, as the torsion returning force of the thin sheet-like member 2 to return to the original plate shape, which force is greater than the elastic returning force of the body 1 at the tip portion 2b of the thin sheet-like member 2, is applied to the opening 1d, large orifices are formed, as shown in the drawing. This state corresponds to a curved portion within the range of from 60 mmHg to 0 mmHg of the characteristic curve A in FIG. 4 which indicates a sudden change in orifice opening area. As a result, for example, if the cuff venting ability is rapidly decreased as the cuff pressure decreases from 60 mmHg, constant cuff venting becomes possible.

The characteristic curve B shows the change in orifice opening area produced when the thin sheet-like member 2 is not twisted.

Figure 5:
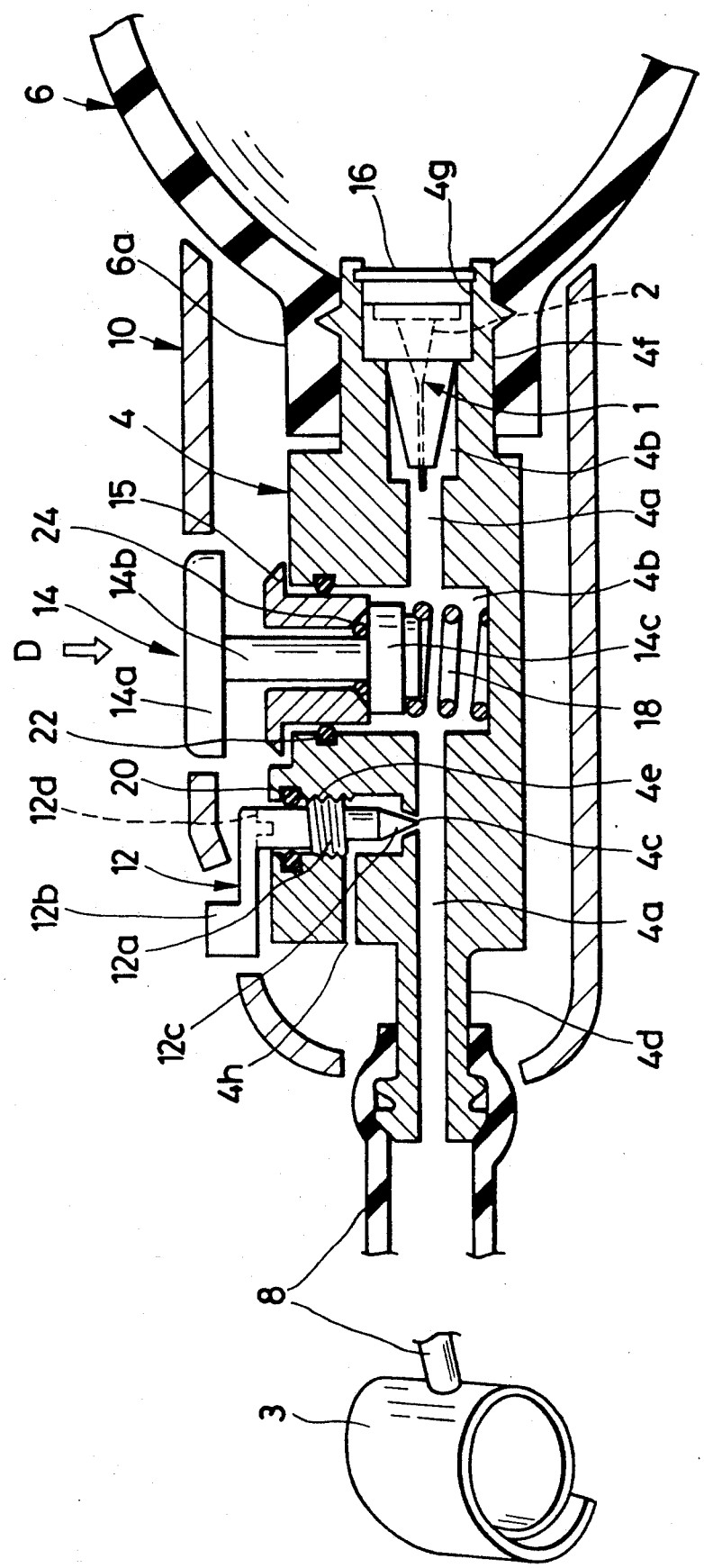
FIG. 5 is a sectional view taken along the center of a sphygmomanometer air-feeding bulb using a gas flow valve.

FIG. 5 is a sectional view taken along the center of an air-feeding bulb for a sphygmomanometer which uses a gas flow valve. In the drawing, an air-feeding bulb 6 is made of a rubber material and functions as an air-feeding pump for manually feeding air to a cuff 3. As shown in the drawing, the bulb 6 is connected to the cuff 3 through a flexible hose 8 and the passageway 4a formed along the longitudinal direction of a connector body 4. The passageway 4a is formed so as to have openings at both ends thereof. At both openings, are provided a mounting tubing 4d on the outer periphery of which a mounting portion is formed for the hose 8, and a discharge valve mounting portion 4g in which the mounting base 1a of the body 1 of the gas flow valve is set. The discharge valve mounting portion 4g further has a groove which is formed in the internal periphery so that a filter for removing foreign materials contained in the air-feeding bulb 6 is attached to the groove. An air-feeding bulb mounting tubing 4f is provided on the outer periphery of the discharge valve mounting portion 4g so that the fitting portion 6a of the air-feeding bulb 6 is fixed, as shown in the drawing.

A vertical hole 4b is formed at right angles to the passageway 4a so that a forced discharge valve 14 for manually forcing air to discharge is disposed therein. As shown in the drawing, the forced discharge valve 14 comprises a movable portion in which a button portion 14a, a shaft portion 14b and a mounting portion 14c are integrally formed; a coil spring 18 for applying to the movable portion an urging force for returning the movable portion to the position shown in the drawing; and a holder 15 having an O-ring 22 provided on the outer periphery thereof for the purpose of holding the movable portion in the vertical hole 4b and keeping an airtight state and an O-ring 24 provided at the internal end thereof. When the movable portion is pushed in the direction shown by the arrow D, the passageway 4a is cause to communicate with the atmosphere, and the airtight state shown in the drawing is usually maintained.

As shown in the drawing, a throttle valve 12 has an external thread portion 12a which is formed in a part of the external periphery thereof so as to be screwed into an internal thread portion 4e formed in the connector body 4. The throttle valve 12 also has a lug portion 12b which is formed in the upper portion thereof so that the throttle valve 12 can be operated form the outside. The movable portion of the throttle valve 12 has a conical or warhead-like needle portion 12c which is integrally formed at the tip thereof and which is inserted into an aperture 4c opened to an air hole 4h opened to the atmosphere so that the discharge orifice can be controlled. The movable portion maintains an airtight state by using an O-ring 20 and cannot be rotated once the throttle valve is set. The movable portion may be provided with the screw portion 12d shown by a broken line in the drawing so that the screw portion 12d can be adjusted by using a driver or the like. A cover 10 is provided for making a beautiful appearance and protecting the members.

Figure 6:
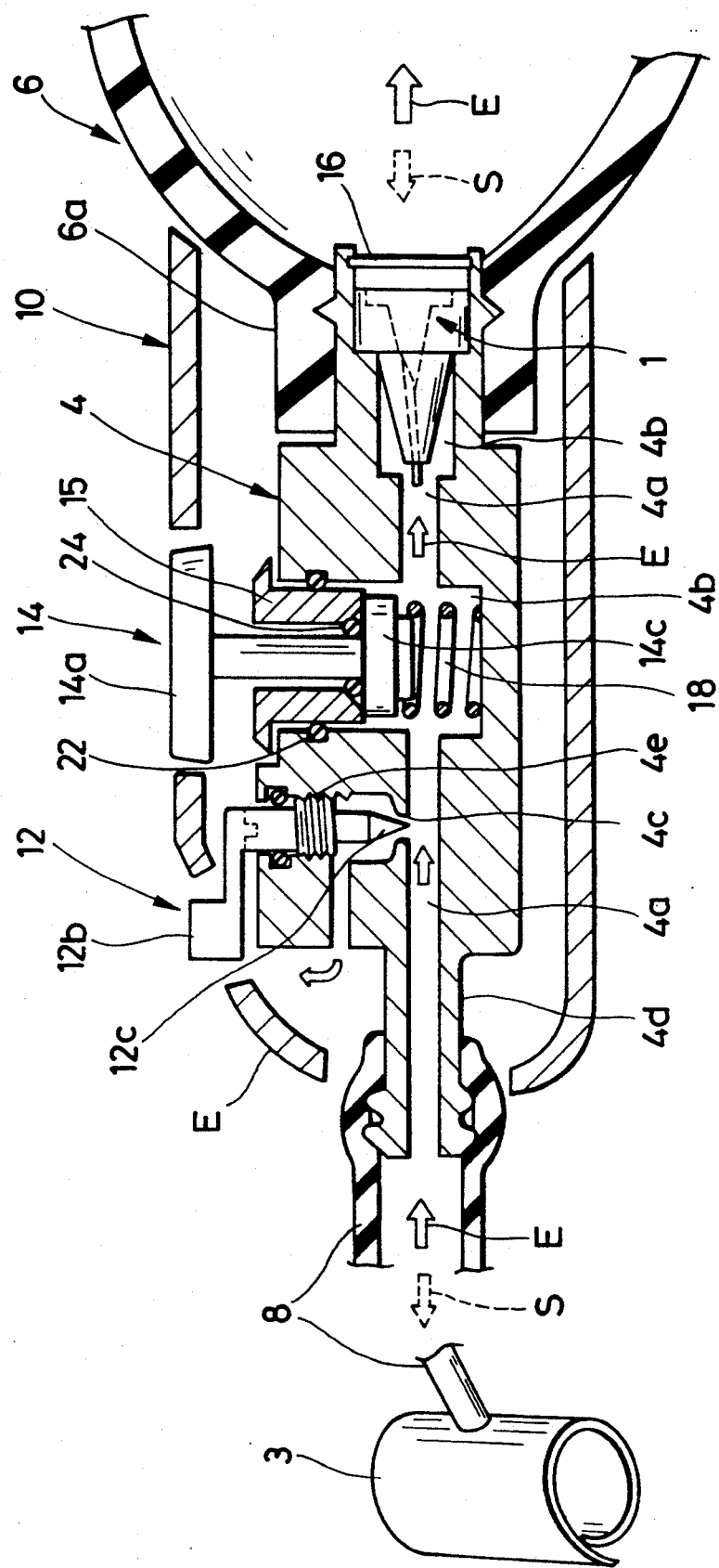
FIG. 6 is a sectional view taken along the center of a sphygmomanometer air-feeding bulb using a gas flow valve and showing the operation thereof.

FIG. 6 is a sectional view taken along the center of the aforementioned sphygmomanometer air-feeding bulb using the gas flow valve for explaining the operation thereof. When a cuff 3 is wrapped around the upper arm at the starting state of measurement where the pressure in the cuff 3 is about 0 mmHg, air is fed in the arrow direction S shown by a broken line by compressing the air-feeding bulb 6 with the hand, with the cuff pressure being increased to about 250 mmHg at the highest.

Blood pressure is measured by reducing the cuff pressure from about 250 mmHg at the highest.

During the pressure reduction, air is discharged from the cuff 3 within the pressure range of 250 mmHg to 60 mmHg through the orifice formed by the needle portion 12c of the throttle valve 12 and the aperture portion 4c of the connector body 4 in the direction denoted by the arrow E. When the discharge proceeds until the cuff pressure becomes 60 mmHg or less and when the venting ability of the cuff 3 significantly deteriorates, since the discharge valve assumes the state shown in FIG. 3C, air is discharged through both the orifice formed by the aperture portion 4c and the discharge valve of the body 1. As a result, venting can be made at a constant rate. The sphygmomanometer air-feeding bulb can be therefore applied to cuffs 3 having various shapes and specifications.

Figure 7:
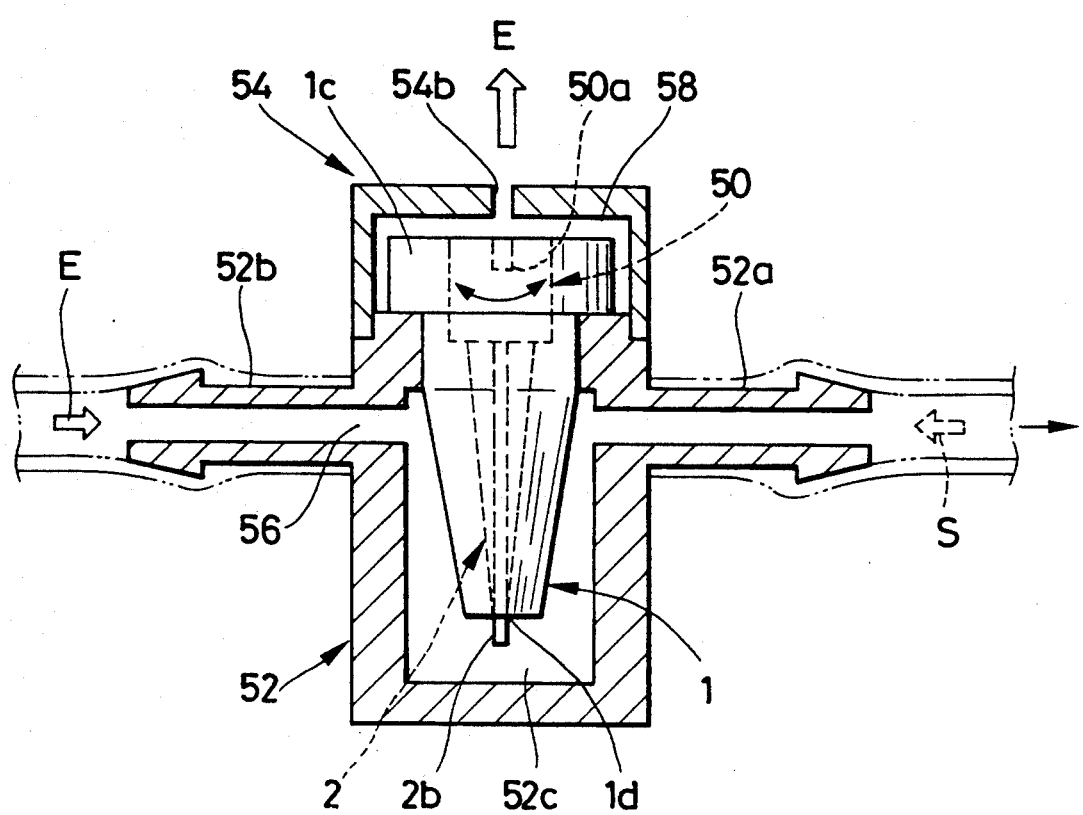
FIG. 7 is a partially broken-out sectional view taken along a line passing through the central surface of gas flow valve of another embodiment according to the present invention.
Figure 8:
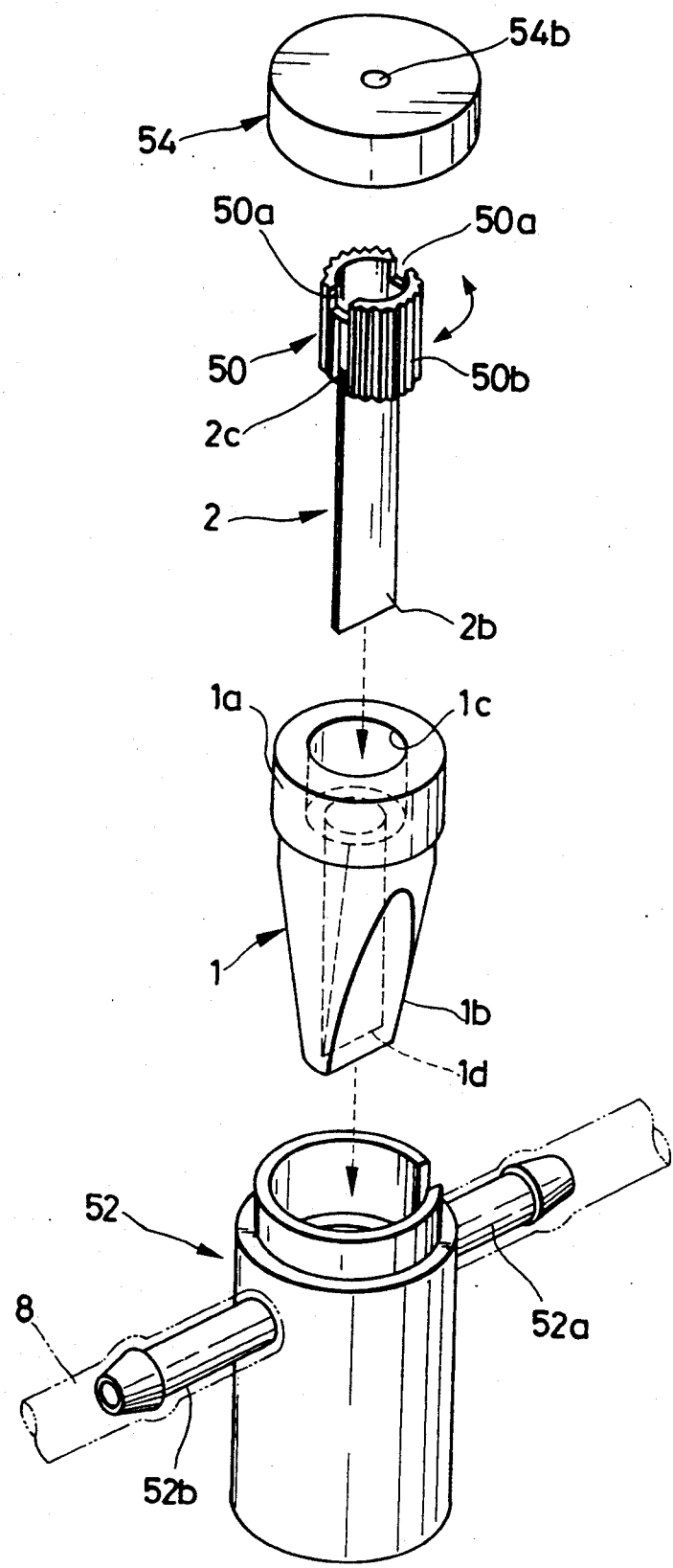
FIG. 8 is a perspective exploded drawing of the gas flow valve shown in FIG. 7.

FIG. 7 is a partially broken-out sectional view taken along a line passing through the central surface of a gas flow valve of another embodiment according to the present invention. FIG. 8 is a perspective exploded view of the gas flow valve shown in FIG. 7. In both drawings, the basic structure is denoted by the same reference numerals as those in FIG. 2. The same portions as those in FIG. 2 are not described below, and different portions only are described below. The air passageway 1c communicating with the opening 1d, which forms the orifices of the body 1, is formed so as to be open at one end thereof in the mounting base 1a, as shown in the drawings.

The thin sheet-like member 2 used in combination with the body 1 can be formed by cutting out the outline from a resin thin sheet having spring properties which allow appropriate torsional deformation, phosphor bronze thin sheet or a stainless thin sheet used for springs. However, a resin thin sheet having low elasticity compared to the thickness is preferable because it is desired that stress is not much changed by twisting the thin sheet.

If the material used for the thin sheet-like member 2 has heat resistance (high softening temperature), a decrease in accuracy is caused to a low extent by a change in elasticity owing to thermal deformation. The thin sheet-like member 2 is formed by machining into the rectangular shape shown in FIG. 8 and then securely held at the upper end portion 2c thereof by the lower end surface of a cylindrical fitting member 50. The fitting member 50 has an air passageway therethrough. The outside dimensions of the fitting member 50 are to some extent greater than the inside dimensions of the air passageway 1c. The fitting member 50 is knurled in a form with lines longitudinally extending for the purpose of preferably maintaining a fixed state of the member 50, which is press-fitted in the air passageway 1c, by frictional force. The fitting member 50 also has two recessed portions 50a which are formed at the upper end thereof for rotating the member 50 by using a minus driver. When the thus-formed fitting member 50 is downwardly inserted (press-fitted) in the air passageway 1c, the assembly shown in FIG. 7 is obtained.

Since the fitting member 50 fitted as described above is held in a state where the inside dimensions of the air passageway 1c of the body 1 made of a rubber material or the like are increased, although the fitting member 50 can be pivotably rotated in the direction shown by the arrow, it can be stopped at a position to which it is rotated, by the elastic force of the passageway 1c to return to the original inside dimensions.

A container body 52 for receiving the body 1 is made of a hard resin material and receives the body 1, as shown in the drawings. The container body 52 comprises nipples 52a, 52b so that it can be singly used as a constant rate pressure reducing valve.

Namely, as shown in FIG. 7, a first passageway 56 opened to a first air chamber 52c of the body 1 is provided in the nipple 52b provided in the container 52, a second passageway being provided in the nipple 52a.

A second air chamber 58 is open to the atmosphere through the hole 54b formed in a cover body 54. The body 1 is contained in the container body 52, and the cover body 54 is then fitted for preventing the body 1 from slipping off from the container to complete the assembly.

In the above arrangement, the thin sheet-like member 2 provided integrally with the fitting member 50 is fitted so as to provide the opening 1d with any desired torsion. Namely, the thin sheet-like member 2 is held at any desired torsion angle so that the opening 1d forming the orifices can be adjusted.

An air-feeding bulb is connected to the nipple 52a of the gas flow valve configured as described above through the hose shown by a two-dot chain line in the drawings. On the other hand, a cuff is connected to the nipple 52b through the hose shown by a two-dot chain line in the drawings. As a result, air is fed from the air-feeding bulb in the direction shown by the arrow S and discharged at a constant rate in the direction shown by the arrow E when the cuff pressure is reduced during measurement of blood pressure.

Figure 9:
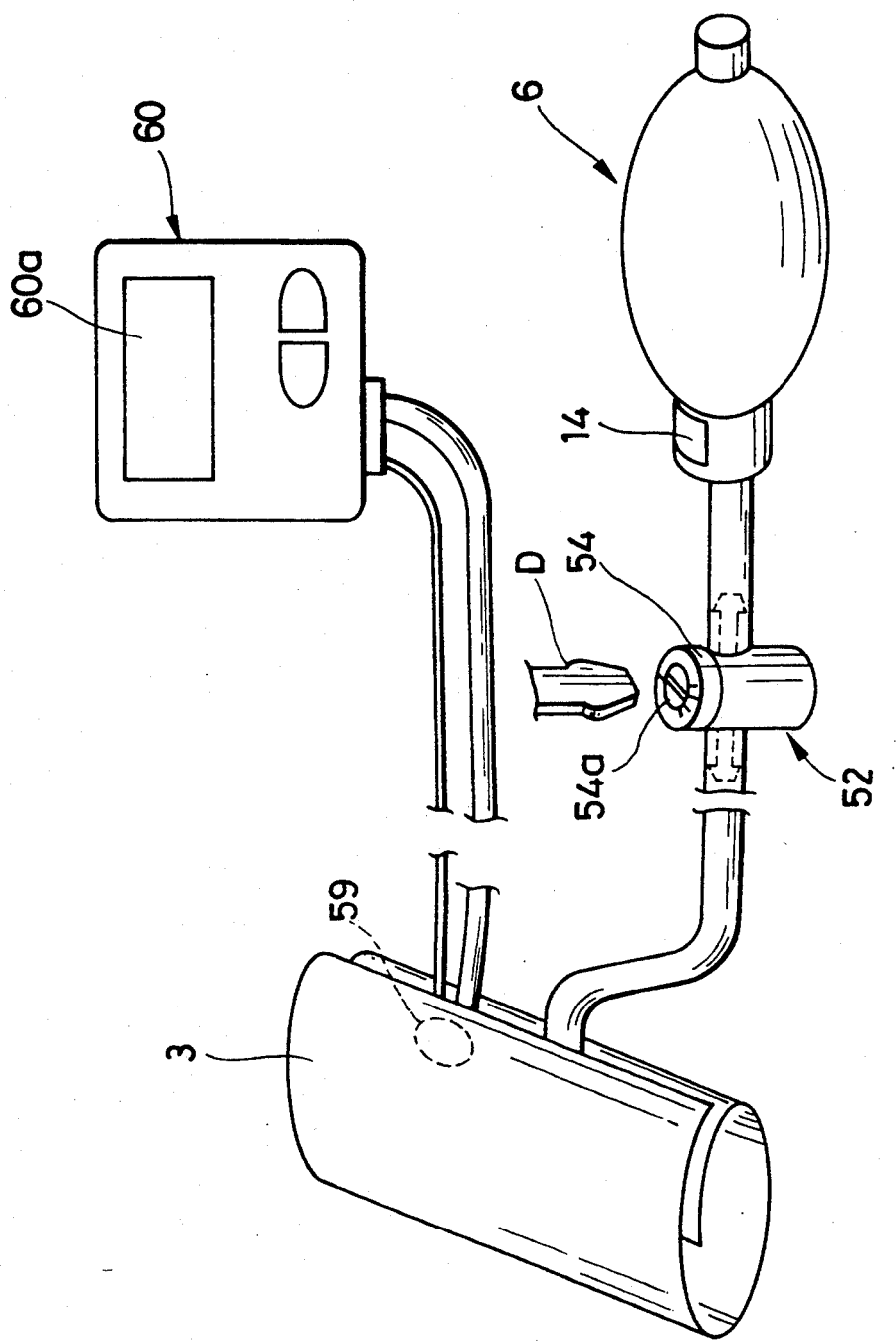
FIG. 9 is a drawing showing an example of a system using the gas flow valve shown in FIG. 8.
Figure 10:
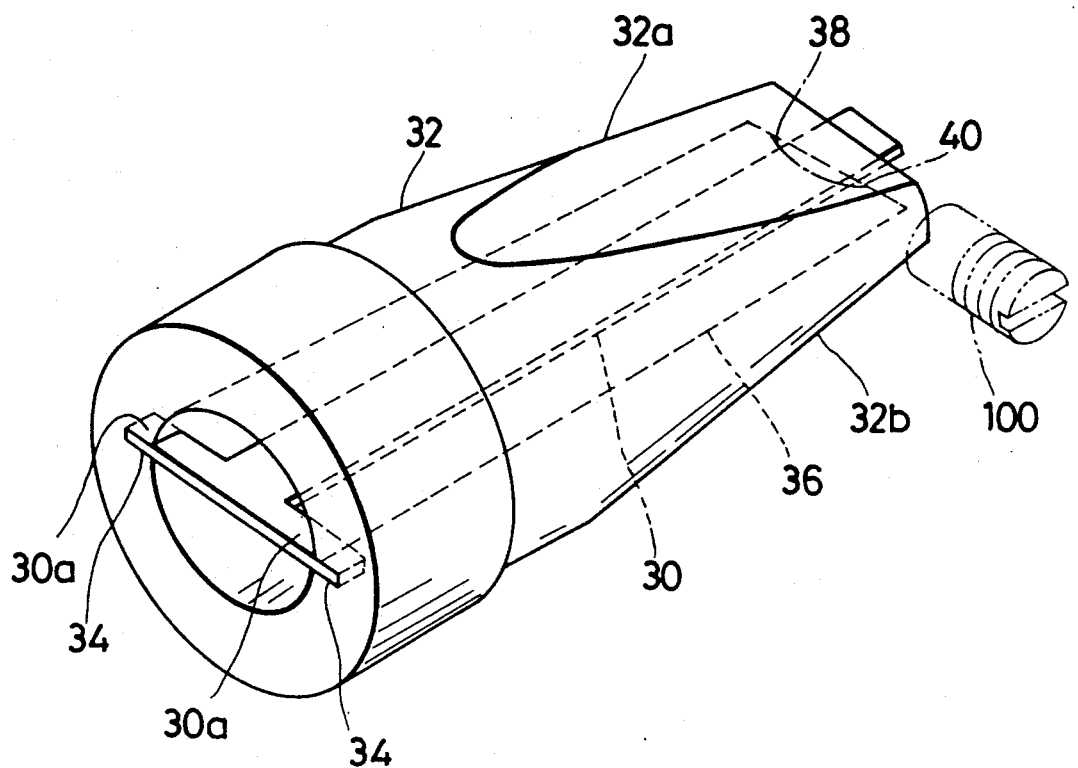
FIG. 10 is a perspective view of the appearance of a prior-art gas flow valve filed by the present applicant.

FIG. 9 is a drawing showing an example of arrangement which uses the gas flow valve shown in FIG. 8. In the drawing, a sensor 59 is contained in any one of cuffs 3 having different sizes, and a sphygmomanometer body 60 is connected to the cuff 3 through tubing and wiring so that blood pressure is measured by a known method of detecting Korotkoff sounds.

On the other hand, the gas flow valve described above with reference to FIGS. 7 and 8 is connected between the air-feeding bulb 6, on which the discharge valve 14 is integrally provided, and the cuff 3 in such a manner that the container 52 is exposed to air, as shown in the drawing. The thus-connected gas flow valve may be provided with an adjustment portion 54a graduated around the hole 54b which is formed in the cover body 54 so as to be open to the atmosphere. Namely, the fitting member 50 is rotated by using a minus driver D the tip of which is inserted into the hole of the adjustment portion 54a and engaged with the recessed portions 50a so that the torsion angle of the thin sheet-like member 2 can be adjusted to any desired value. When such an adjustment portion 54a is not provided, the torsion angle is adjusted by using a minus driver in a state where the cover body 54 is removed, and the cover body 54 is then fitted.

The gas flow valve disposed as described above is capable of absorbing the scattering in compliance, which is attributed to the air capacity and material of the cuff used. In addition, when the gas flow valve is contained in the cuff 3, it is possible to prevent any foreign body sensation during fitting of the cuff 3 and any influence of stress during an increase in cuff pressure.

As described above, the present invention can provide a gas flow valve which can be used with a cuff showing a rapid decrease in venting ability at a predetermined pressure value at a boundary within the pressure range, which allows measurement of blood pressure, and which valve enables constant venting.

The present invention can further provide a sphygmomanometer air-feeding/discharging apparatus which has flexibility for cuffs having various shapes and specifications and which allows easy adjustment of the orifice area.

The present invention can provide a gas flow valve which allows easy adjustment of the orifice area.

The present invention can provide a air-feeding/discharging apparatus which conforms to the pressure reduction characteristics of cuffs in various levels of compliance.

What is claimed is:
1. A gas flow valve comprising:
a body made of an elastic material and comprising a mounting base portion, a wedge-shaped portion formed integrally with said mounting base portion and having a flat portion with upper and lower surfaces serving as pressure-responsive surfaces, a linear opening formed in a tip portion of said wedge-shaped portion, and a passageway extending in a lengthwise direction in said mounting base portion and said wedge-shaped portion and communicating with said opening;
a thin sheet-like member having a tip portion and a rear end fitting portion and disposed in said passageway such that said tip portion of said sheet-like member is held by said opening; and
means for coupling said rear end fitting portion with said mounting base portion of said body for holding said thin sheet-like member in a twisted state in said passageway; and wherein elastic deformation of a gas passageway formed by gaps in said opening during pressure reduction is promoted by resiliency of torsion of said twisted thin sheet-like member.

2. An air feeding/discharging apparatus for a sphygmomanometer for feeding air to and discharging air from a cuff, comprising:

an air-feeding bulb having an air-feeding outlet;

a gas flow valve according to claim 1 which is coupled between said cuff and the air-feeding outlet of said air-feeding bulb;

a discharge valve coupled to said cuff and said gas flow valve for forcing air to discharge in a manual manner; and a throttle valve interposed between said cuff and said discharge valve for gradually reducing cuff pressure during measurement of blood pressure and for adjusting a rate of pressure reduction.

3. An air feeding/discharging apparatus for a sphygmomanometer according to claim 2, further comprising:

a connector means attached to said air-feeding bulb;

said connector means incorporating said gas flow valve, said discharge valve and said throttle valve therein; and said connector means being attached to said cuff.

4. An air feeding/discharging apparatus for a sphygmomanometer according to claim 3, further comprising:

cover means which covers said connector means and which allows operating portions of said discharge valve and said throttle valve to appear therethrough.

5. The air feeding/discharging apparatus according to claim 2, wherein said rear end fitting portion of said thin sheet-like member comprises a fitting member integrally connected with said thin sheet-like member and securely fitted in an opening of said mounting base portion of said body and being engaged with said mounting base portion of said body for holding said thin sheet-like member in said twisted state in said passageway.

6. The air feeding/discharging apparatus according to claim 5, wherein said fitting member has a passageway therein which is opened at one end thereof, and which also communicates with said passageway which extends in said lengthwise direction in said body.

7. The air feeding/discharging apparatus according to claim 5, further comprising means for adjusting a rotational position of said fitting member within said mounting base portion for varying the amount of twisting of said thin sheet-like member within said body.

8. A gas flow valve according to claim 1, wherein said body is made of silicone rubber.

9. A gas glow valve according to claim 1, wherein said thin sheet-like member is made of a resin sheet having heat resistance.

10. A gas flow valve according to claim 1, wherein said thin sheet-like member is made of a metal sheet which has elasticity.

11. A gas flow valve according to claim 1, wherein said rear end fitting portion of said thin sheet-like member comprises a fitting member integrally connected with said thin sheet-like member and securely fitted in an opening of said mounting base portion of said body and being engaged with said mounting base portion of said body for holding said thin sheet-like member in said twisted state in said passageway.

12. A gas flow valve according to claim 11, wherein said fitting member has a passageway therein which is opened at one end thereof, and which also communicates with said passageway which extends in said lengthwise direction in said body.

13. A gas flow valve according to claim 11, further comprising means for adjusting a rotational position of said fitting member within said mounting base portion for varying the amount of twisting of said thin sheet-like member within said body.

14. A gas flow valve comprising:

a body comprising a mounting base portion, a tip base portion formed integrally with said mounting base portion and having a wedge-like outer shape and a flat portion with upper and lower surfaces serving as pressure-responsive surfaces, a linear opening formed in a tip end portion of said tip base portion, a first passageway communicating with said opening and extending in a longitudinal direction within said mounting base portion and said tip base portion, and a fitting hole opened at one end thereof at a rear end portion of said mounting base portion; and a thin sheet-like member provided integrally with a fitting member which is securely fitted into said fitting hole, said fitting member having a second passageway opened at one end thereof and communicating with said first passageway at another end thereof; and wherein when said thin sheet-like member is disposed in said first passageway in a twisted state, said fitting member fitted in said fitting hole can be freely rotated in the direction of a torsion angle so that a torsion angle of twisting of said thin sheet-like member can be adjusted.

15. A gas flow valve according to claim 14, wherein said thin sheet-like member comprises a resin sheet having heat resistance.

16. A gas flow valve according to claim 15, wherein, in order to enable the adjustment of the torsional angel of said thin sheet-like member twisted and held by said opening, a frictional fitting surface is formed in the external periphery of said fitting member, and recessed portions are formed at the end surface of said fitting member opposite to the side, to which said thin sheet-like member is attached, so that said torsional angle can be adjusted by applying a rotational force to said recessed portions.

17. A sphygmomanometer air-feeding/discharging apparatus comprising a gas flow valve of claim 15 and an air-feeding bulb in fluid communication with one another for feeding and discharging air to and from a cuff.

18. A gas flow valve according to claim 14, wherein, in order to enable the adjustment of the torsional angle of said thin sheet-like member twisted and held by said opening, a frictional fitting surface is formed in the external periphery of said fitting member, and recessed portions are formed at the end surface of said fitting member opposite to the side to which said thin sheet-like member is attached, so that said torsion angle can be adjusted by applying a rotational force to said recessed portions.

19. A sphygmomanometer air-feeding/discharging apparatus comprising a gas flow valve of claim 18 and an air-feeding bulb in fluid communication with one another for feeding and discharging air to and from a cuff.

20. A sphygmomanometer air-feeding/discharging apparatus comprising a gas flow valve of claim 14 and an air-feeding bulb in fluid communication with one another for feeding and discharging air to and from a cuff.

* * * * *

UNITED STATES PATENT AND TRADEMARK OFFICE
CERTIFICATE OF CORRECTION

PATENT NO.   : 5,137,024
DATED        : August 11, 1992
INVENTOR(S)  : SOUMA, Takahiro It is certified that error appears in the above-identified patent and that said Letters Patent is hereby corrected as shown below:

Column 10, Claim 16:

Line 47 - change "side," to --side--.

Line 48 - change "torsional" to --torsion--.

Signed and Sealed this

Twelfth Day of October, 1993

Attest:

BRUCE LEHMAN

Attesting Officer

Commissioner of Patents and Trademarks